United States Patent
Wieczorek et al.

(10) Patent No.: US 9,777,214 B2
(45) Date of Patent: Oct. 3, 2017

(54) GARNET SCINTILLATOR COMPOSITION

(71) Applicant: KONINKLIJKE PHILIPS N.V., Eindhoven (NL)

(72) Inventors: Herfried Karl Wieczorek, Aachen (DE); Cornelis Reinder Ronda, Aachen (DE); Jacobus Gerardus Boerekamp, Someren (NL); Anne-Marie Andree Van Dongen, Waalre (NL); Sandra Johanna Maria Paula Spoor, Eindhoven (NL); Daniela Buettner, Aachen (DE); Wilhelmus Cornelis Keur, Weert (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/915,282

(22) PCT Filed: Dec. 16, 2014

(86) PCT No.: PCT/EP2014/077856
§ 371 (c)(1),
(2) Date: Feb. 29, 2016

(87) PCT Pub. No.: WO2015/106904
PCT Pub. Date: Jul. 23, 2015

(65) Prior Publication Data
US 2016/0312117 A1 Oct. 27, 2016

Related U.S. Application Data

(60) Provisional application No. 61/916,963, filed on Dec. 17, 2013.

(30) Foreign Application Priority Data

Feb. 27, 2014 (EP) ................................. 14157017

(51) Int. Cl.
*A61K 9/00* (2006.01)
*C09K 11/77* (2006.01)
(Continued)

(52) U.S. Cl.
CPC .......... *C09K 11/7774* (2013.01); *A61K 51/00* (2013.01); *G01T 1/2018* (2013.01); *G01T 1/2023* (2013.01); *G01T 1/2985* (2013.01)

(58) Field of Classification Search
CPC .................................................. C09K 11/7774
See application file for complete search history.

(56) References Cited

U.S. PATENT DOCUMENTS 6,630,077 B2   10/2003   Shiang et al.
6,793,848 B2   9/2004   Vartuli et al.
(Continued)

FOREIGN PATENT DOCUMENTS

DE   102013103783   10/2013
EP   463369        1/1992
(Continued)

OTHER PUBLICATIONS

Machine translation of JP 2012-180399 to Furukawa, Nov. 26, 2016.*
(Continued)

*Primary Examiner* — Paul Dickinson (57) ABSTRACT

A ceramic or polycrystalline scintillator composition is represented by the formula $(Lu_yGd_{3-y})(Ga_xAl_{5-x})O_{12}$:Ce; wherein $y=1\pm0.5$; wherein $x=3\pm0.25$; and wherein Ce is in the range 0.01 mol % to 0.7 mol %. The scintillator composition finds application in the sensitive detection of ionizing radiation and may for example be used in the detection of gamma photons in the field of PET imaging.

18 Claims, 6 Drawing Sheets

| Compound | relative light yield ( % ) | $\tau_1$ ( ns ) | CRT ( ps ) |
|---|---|---|---|
| Single crystal $Gd_3Ga_3Al_2O_{12}$ ( PRIOR ART ) | 100 % | 100 - 110 | 980 - 1050 |
| Ceramic $Lu_1Gd_2Ga_3Al_2O_{12}$ ( INVENTION ) | 82 % | 45 - 47 | 650 - 750 |

(51) Int. Cl.
*A61K 51/00* (2006.01)
*G01T 1/20* (2006.01)
*G01T 1/202* (2006.01)
*G01T 1/29* (2006.01)

(56) References Cited

U.S. PATENT DOCUMENTS

| | | |
|---|---|---|
| 7,252,789 B2 | 8/2007 | Venkataramani et al. |
| 7,595,492 B2 | 9/2009 | Nakamura et al. |
| 8,969,812 B2 | 3/2015 | Yoshikawa et al. |
| 2005/0093431 A1 | 5/2005 | Hancu et al. |
| 2006/0251312 A1* | 11/2006 | Krieg ............... A61B 6/037 382/131 |
| 2010/0294939 A1 | 11/2010 | Kuntz et al. |
| 2012/0153165 A1* | 6/2012 | Ott ............... G01T 1/2935 250/362 |
| 2015/0275080 A1 | 10/2015 | Ronda et al. |

FOREIGN PATENT DOCUMENTS

| | | |
|---|---|---|
| EP | 1162635 | 12/2001 |
| JP | 2012180399 | 9/2012 |
| JP | 2013002882 | 1/2013 |

OTHER PUBLICATIONS

Takanori Endo, et al., "Scintillation properties of Ce doped (Lu, Gd) 3 (Ga,Al) 5 0 12 single crystal grown by the micro-puling-down method", Nuclear Science Symposium and Medical Imaging Conference (NSS/MIC) 2011 IEEE.

Kei Kamada, et al., "Composition Engineering of Cerium-Doped (Lu,Gd) 3 (Ga,Al) 5 0 12 Single-Crystal Scintillators" Crystal Growth & Design, vol. 11, No. 10, Oct. 5, 2011.

C. Ronda "Luminescence: From Theory to Applications", Wiley-VCH, Darmstadt, 2007.

\* cited by examiner

| Compound | light yield (photons/ MeV) | $\tau_1$ (ns) | $\tau_2$ (ns) |
|---|---|---|---|
| $Gd_3Ga_2Al_3O_{12}$ | 45 931 | 221 (100%) | |
| $Gd_3Ga_3Al_2O_{12}$ | 42 217 | 52.8 (73%) | 282 (27%) |
| $Gd_3Ga_4Al_1O_{12}$ | 17 912 | 42.2 (34%) | 90.5 (66%) |
| $Lu_1Gd_2Ga_2Al_3O_{12}$ | 30 627 | 75.7 (38%) | 326 (62%) |
| $Lu_1Gd_2Ga_3Al_2O_{12}$ | 18 166 | 50.7 (65%) | 298 (35%) |

PRIOR ART FIG. 1

| Compound | relative light yield (%) | $\tau_1$ (ns) | CRT (ps) |
|---|---|---|---|
| Single crystal $Gd_3Ga_3Al_2O_{12}$ (PRIOR ART) | 100 % | 100 - 110 | 980 – 1050 |
| Ceramic $Lu_1Gd_2Ga_3Al_2O_{12}$ (INVENTION) | 82 % | 45 - 47 | 650 - 750 |

FIG. 2

| Compound | Photopeak absorption (%) based on MC analysis for 21.5 mm scintillator element length | Photopeak absorption (%) based on MC analysis for 25.0 mm scintillator element length |
|---|---|---|
| $Gd_3Ga_2Al_3O_{12}$ | 60 | 71 |
| $Lu_1Gd_2Ga_2Al_3O_{12}$ | 72 | 84 |
| $Lu_2Gd_1Ga_2Al_3O_{12}$ | 87 | 100 |
| $Lu_3Ga_2Al_3O_{12}$ | 99 | 100 |

FIG. 3A

| Compound | Light yield (arb. units) |
|---|---|
| Ceramic $Lu_{0.3}Gd_{2.7}Ga_{2.5}Al_{2.5}O_{12}$ | 1230 - 1480 |
| Ceramic $Lu_1Gd_2Ga_2Al_3O_{12}$ | 1190 |
| Ceramic $Lu_2Gd_1Ga_2Al_3O_{12}$ | 1120 |

FIG. 3B

| Compound | Light yield (arb. units) | $\tau_1$ (ns) | Light yield/$\tau_1$ |
|---|---|---|---|
| Ceramic $Lu_1Gd_2Ga_2Al_3O_{12}$ | 1190 | 171 | 7.0 |
| Ceramic $Lu_1Gd_2Ga_{2.5}Al_{2.5}O_{12}$ | 1180 | 97 | 12.3 |
| Ceramic $Lu_1Gd_2Ga_{2.75}Al_{2.25}O_{12}$ | 1175 | 68 | 17.3 |
| Ceramic $Lu_1Gd_2Ga_3Al_2O_{12}$ | 1160 | 47 - 58 | ~22 |

FIG. 4

| Compound | Light yield (arb. units) | $\tau_1$ ( ns ) |
|---|---|---|
| Ceramic $Lu_1Gd_2Ga_3Al_2O_{12}$ :Ce with 0.1 mol % Ce | 995 - 1060 | 48 - 55 |
| Ceramic $Lu_1Gd_2Ga_3Al_2O_{12}$ :Ce with 0.2 mol % Ce | 1000 - 1400 | 47 - 55 |
| Ceramic $Lu_1Gd_2Ga_3Al_2O_{12}$ :Ce with 0.4 mol % Ce | 1070 - 1160 | 57 - 58 |

| Compound | τ₁ (ns) | Light Yield (% relative to LYSO) | Extrapolated photon gain relative to day 10( % ) at time = 10 years | CRT (ps) |
|---|---|---|---|---|
| Ceramic $Lu_1Gd_2Ga_3Al_2O_{12}$ :Ce with 0.05 mol % Ce | 40 – 44 | 88 | 94 – 95 | 665 – 675 |
| Ceramic $Lu_1Gd_2Ga_3Al_2O_{12}$ :Ce with 0.1 mol % Ce | 41 – 48 | 82 – 88 | 95 – 98.5 | 710 – 745 |
| Ceramic $Lu_1Gd_2Ga_3Al_2O_{12}$ :Ce with 0.2 mol % Ce | 46 – 55 | 66 – 77 | 80 – 82 | 665 – 700 |
| Ceramic $Lu_1Gd_2Ga_3Al_2O_{12}$ :Ce with 0.4 mol % Ce | 57 – 58 | 61 - 74 | 50 – 60 | 740 – 750 |

FIG. 11

GARNET SCINTILLATOR COMPOSITION

CROSS REFERENCE TO RELATED APPLICATIONS

This application is the U.S. National Phase application under 35 U.S.C. §371 of International Application No. PCT/EP2014/077856, filed Dec. 16, 2014, published as WO 2015/106904 on Jul. 23, 2015, which claims the benefit of U.S. Provisional Patent Application No. 61/916,963 filed Dec. 17, 2013 and European Patent Application No. 14157017.6 filed Feb. 27, 2014. These applications are hereby incorporated by reference herein.

FIELD OF THE INVENTION

The invention relates to a garnet scintillator composition for use in the detection of ionizing radiation. The invention finds particular application in the detection of gamma photons and may be used in the field of PET imaging.

BACKGROUND OF THE INVENTION

Scintillator compositions used in the detection of ionizing radiation respond to the reception of an energetic photon by generating a pulse of scintillation light. The energetic photon may for example be an x-ray or gamma photon, and the resulting light pulse typically comprises a plurality of optical photons having wavelengths in the infrared to ultraviolet spectral range. The scintillation light pulse is conventionally detected using an optical detector which generates an electrical pulse at its output that may subsequently be processed by electronic circuitry. Together, a scintillator composition that is optically coupled to an optical detector, referred to herein as an ionizing radiation detector, may be configured to receive energetic photons from the imaging region of for example a PET or a SPECT imaging system. In such an imaging system the received energetic photons provide data for subsequent reconstruction into an image indicative of radioactive decay events in the imaging region. Ionizing radiation detectors may likewise be used to detect energetic photons traversing the imaging region of a CT imaging system.

The selection of a scintillator composition for use in such ionizing radiation detectors is subject to a variety of constraints imposed by the imaging system in which the detector is to be used. A PET imaging system may be considered to impose some of the most stringent limitations on such scintillator compositions owing to the need to accurately time the reception of each individual gamma photon, and the need to determine its energy. The time of reception of each gamma photon is important in the identification of coincident pairs of gamma photons, which by virtue of their detection within a narrow time interval are interpreted as having been generated by a radioactive decay event that lies along a line in space between their detectors, termed a line of response. The energy of each gamma photon may be further used to confirm whether timewise-coincident pairs of gamma photons share a common origin along the line of response by discarding pairs of events in which one of the gamma photons has undergone energy-altering scattering. Coincident pairs of gamma photons each having an energy that is within a predetermined narrow range are interpreted as being the product of a single radioactive decay event. The energy of each gamma photon is typically determined by integrating the light pulse, or by counting the number of scintillation photons produced by each gamma photon.

These requirements manifest themselves in the need for a scintillator composition with a high light yield and a short decay time. The high light yield improves the signal to noise ratio at the output of the optical detector, and the short decay time is important in the prevention of pile-up. Pile-up occurs when the scintillation light pulse from a gamma photon overlaps in time with the scintillation light pulse generated by a previously-received gamma photon. Pile-up degrades both the timing accuracy of a gamma photon detector and the ability to determine the energy of each gamma photon.

The light yield of a scintillator composition, measured in units of photons per MeV, is a measure of the number of scintillation photons produced in response to a received energetic photon. A high light yield is achieved by using a scintillator composition with strong photopeak absorption. The decay time of a scintillator composition is conventionally determined by fitting the decay of the scintillation light pulse with two time constants. A primary decay constant accompanied by the percentage of the total scintillation light emitted during the primary decay period extrapolated to infinity models the initial decay, and this is followed by a secondary decay constant that is likewise accompanied by the percentage of the total scintillation light emitted during the secondary decay period extrapolated to infinity. Thus, the light yield, and the decay time, comprising its primary and secondary components, are two parameters that affect the sensitivity of a scintillator composition.

A PET imaging system typically comprises an imaging region, around which are disposed a plurality of ionizing radiation detectors, or more specifically, gamma radiation detectors, which in combination with timing circuitry are configured to time the reception of gamma photons. The gamma photons may be produced following the decay of a radiotracer within the imaging region. Pairs of gamma photons that are detected within a time interval of typically +/−3 ns of each other are deemed coincident and are interpreted as having been generated along a line of response (LOR) between their two gamma radiation detectors. Multiple lines of response are subsequently used as the data input to a reconstruction processor executing reconstruction algorithms to reconstruct an image indicative of the radiotracer distribution within the imaging region.

The timing certainty associated with the detection of a pair of gamma photons in a PET imaging system is determined by its coincidence resolving time, or CRT. The CRT is the narrowest time interval within which two gamma photons received simultaneously by different gamma photon detectors are certain to have been detected. A coincidence resolving time of less than +/−3 ns is typically desirable in a PET imaging system in order to be assign their detection to a 90 cm LOR. This corresponds to approximately the maximum typical bore diameter of a PET imaging system. In a PET imaging system having a CRT of shorter than +/−3 ns, an estimate of the originating position of a pair of gamma photons along the line of response may further be determined based on the exact times of detection of two gamma photons. A shorter CRT permits the reconstruction processor in such an imaging system to reconstruct a more accurate image of the radiotracer distribution within its imaging region. This principle is employed in a Time of Flight (TOF) PET imaging system, in which a CRT of less than +/−3 ns is preferred, and in which a CRT of less than +/−1 ns is even more preferred. The CRT of a PET imaging system is affected by the scintillator decay time, by the probability of gamma photon scattering within the scintillator composition, by the depth of interaction of a gamma photon within the scintillator composition, by the geometry of the scintillator composition, and by the timing accuracy of the electronic timing circuitry. Minimizing the CRT is therefore a key goal in improving the sensitivity of a PET imaging system and this places additional emphasis on using a scintillator composition with a short decay time.

Some known scintillator compositions that are suitable for use in PET imaging systems are disclosed in publication "Luminescence: From Theory to Applications", Wiley-VCH, Darmstadt, 2007, C. Ronda (Ed.). These include LYSO (lutetium yttrium oxy-orthosilicate) crystals and $LaBr_3$ crystals. Scintillation in LYSO has been reported with a light yield of 33000 photons/ MeV in the presence of a decay time of 44 ns. A higher light yield has been reported in $LaBr_3$ in the presence of a decay time of 25 ns. Single crystal compositions are investigated almost exclusively owing to the best combination of stopping power, decay time and light yield being found in single crystal compositions.

Figure 1:
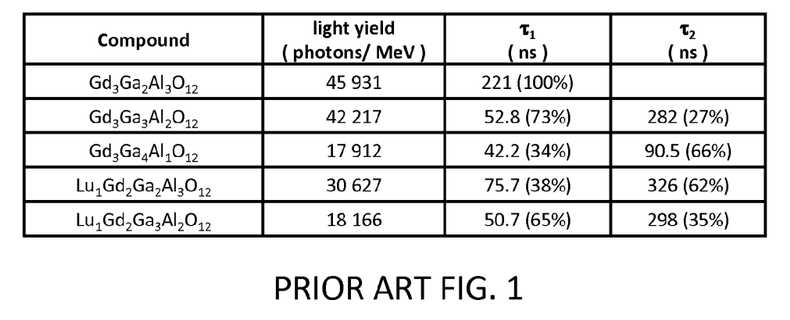
FIG. 1 illustrates the light yield, primary decay constant, and secondary decay constant in various crystal garnet compositions as adapted from publication "Composition Engineering in Cerium-Doped $(Lu,Gd)_3(Ga,Al)_5O_{12}$ Single-Crystal Scintillators", K. Kamada et al, Cryst. Growth Des., 2011, 11 (10), pp 4484-4490.

More recently, garnet crystals have been reported for use as scintillator compositions as disclosed in publication "Composition Engineering in Cerium-Doped $(Lu,Gd)_3(Ga,Al)_5O_{12}$ Single-Crystal Scintillators", K. Kamada et al, Cryst. Growth Des., 2011, 11 (10), pp 4484-4490. According to this publication, the adapted results of which are illustrated in the table in FIG. 1, the light yield of a reference single crystal $Gd_3Ga_2Al_3O_{12}$ garnet composition is significantly reduced from 45931 photons/MeV to 30627 photons/MeV when lutetium is incorporated into the composition to form $Lu_1Gd_2Ga_2Al_3O_{12}$. The light yield in the table in FIG. 1 can also be seen to reduce from 30627 photons/MeV to 18166 photons/MeV when the relative gallium-to-aluminium content is increased. This effect is known in the literature as thermal quenching.

Garnet scintillator compositions are also known from documents US6630077B2, DE102013103783A1, US7252789B2, US6793848B2 and EP463369A1.

The present invention seeks to overcome limitations of known scintillator materials.

SUMMARY OF THE INVENTION

It is an object of the invention to provide a scintillator composition for use in the detection of ionizing radiation with improved sensitivity. Another object of the invention is to provide a scintillator composition with reduced decay time. Another object of the invention is to provide a scintillator composition with improved light yield. Another object of the invention is to provide a scintillator composition with improved stopping power. Another object of the invention is to provide a gamma photon detector with improved sensitivity. Another object of the invention is to provide a PET imaging system with improved CRT.

These objects are achieved by the present application comprising the ceramic or polycrystalline garnet composition represented by the formula $(Lu_yGd_{3-y})(Ga_xAl_{5-x})O_{12}$:Ce; wherein y=1±0.5; wherein x=3±0.25; and wherein Ce is in the range 0.01 mol % to 0.7 mol %.

In accordance with one aspect of the invention the range of the ratio of lutetium to gadolinium in the composition is controlled.

In accordance with another aspect of the invention the range of the ratio of gallium to aluminium is controlled.

In accordance with another aspect of the invention the range of the cerium content in the composition is controlled. Within the controlled range it has been found that the cerium content gives a balance between sufficiently high light yield and a sufficiently short decay time for the scintillator composition to operate as a sensitive scintillator.

In accordance with another aspect of the invention the decay time of the composition is less than or equal to 55 ns. The selected range of the parameter y which affects the ratio of lutetium to gadolinium, the range of the parameter x which affects the ratio of gallium to aluminium, and the cerium range in the composition together give rise to a decay time of less than or equal to 55 ns, and consequently a sensitive scintillator composition.

In accordance with another aspect of the invention the light yield exceeds 30000 photons/MeV. The selected range of the parameter y which affects the ratio of lutetium to gadolinium, the range of the parameter x which affects the ratio of gallium to aluminium, and the cerium range in the composition together give rise to a light yield that exceeds 30000 photons/MeV, and consequently a sensitive scintillator composition.

In accordance with another aspect of the invention a detector for ionizing radiation is provided. The ionizing radiation detector comprises the garnet composition described above in optical communication with an optical detector. In one example implementation the ionizing radiation is gamma radiation and the ionizing radiation detector is a gamma photon detector.

In accordance with another aspect of the invention a PET imaging system is provided. The PET imaging system comprises a plurality of the aforementioned gamma photon detectors. The PET imaging system may alternatively be a TOF PET imaging system.

In accordance with another aspect of the invention a PET imaging system, or a TOF PET imaging system, that includes the garnet scintillator composition described above is provided with a CRT of less than 750 ns. The selected ranges of the ratio of lutetium to gadolinium, the ratio of gallium to aluminium, and the selected range of cerium in the garnet scintillator composition result in a combination of decay time and light yield that give rise to a sensitive imaging system with a CRT of less than 750 ns.

In accordance with another aspect of the invention a method for manufacture of a garnet composition is provided.

DETAILED DESCRIPTION OF THE INVENTION

The garnet scintillator composition of the present invention is described with reference to gamma photon detection in a PET imaging system. However, it is to be appreciated that the invention also finds application in the broader field of ionizing radiation detection, and may for example be used in a CT or a SPECT imaging system.

According to the present invention a ceramic or polycrystalline garnet composition represented by the formula $(Lu_yGd_{3-y})(Ga_xAl_{5-x})O_{12}$:Ce is provided wherein y=1±0.5; wherein x =3±0.25; and wherein Ce is in the range 0.1 mol % to 0.7 mol %. The composition $(Lu_yGd_{3-y})(Ga_xAl_{5-x})O_{12}$ provides a host structure within which the cerium dopant facilitates light emission following the reception of an energetic photon such as a gamma photon. This composition results in part from the realization that the sensitivity of a garnet composition may be improved by controlling its stopping power. The stopping power of a scintillator composition determines its ability to absorb incoming gamma photons within a predetermined thickness. Higher stopping power materials enable the capture of the same proportion of incoming gamma photons within a reduced thickness scintillator composition. The stopping power of a composition increases with its atomic, or z, number. Lutetium, with an atomic number of 71, therefore has a higher stopping power than gadolinium which has an atomic number of 64. In the present invention the parameter y controls the ratio of lutetium to gadolinium and thus the stopping power is increased by increasing the parameter y.

Figure 2:
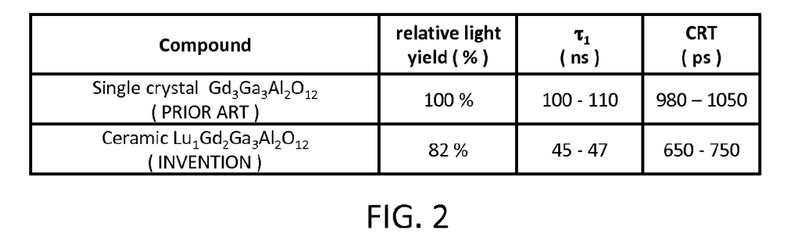
FIG. 2 illustrates a comparison between a ceramic garnet composition according to the present invention $Lu_1Gd_2Ga_3Al_2O_{12}$ thus having y=1 and a prior art single crystal garnet composition $Gd_3Ga_3Al_2O_{12}$ thus having y=0.

FIG. 2 illustrates a comparison between a ceramic garnet composition according to the present invention $Lu_1Gd_2Ga_3Al_2O_{12}$ thus having y=1 and a prior art single crystal garnet composition $Gd_3Ga_3Al_2O_{12}$ thus having y=0. The relative light yield of the ceramic composition in FIG. 2 is 82% of the single crystal reference composition of the prior art. Furthermore, the primary decay constant $\tau_1$ of the ceramic composition is approximately half that of the single crystal composition. The reference single crystal composition used to obtain the results in the table in FIG. 2 was obtained from the FURUKAWA DENSHI Co., Ltd, Marunouchi Nakadori Bldg., Marunouchi 2-chome, Chiyoda-ku, Tokyo, JAPAN, 100-8370 and its measured primary decay constant $\tau_1$ is comparable to the 90 ns value according to the manufacturer's specification. Moreover, when tested in an experimental PET imaging system the CRT of the ceramic composition of the present invention is reduced by some 30% as compared to the CRT measured in the prior art single crystal garnet. The reduced decay time of the ceramic composition illustrated in FIG. 2 demonstrates a significant improvement to the sensitivity of the scintillator composition at the expense of a relatively small, 18%, degradation in light yield. The reduced CRT in the ceramic composition of the present invention as compared to that in the prior art reference single crystal composition indicates improved timing performance and makes the composition of the present invention particularly suitable for use in TOF PET.

However, such a result is unexpected in light of data published in document "Composition Engineering in Cerium-Doped $(Lu,Gd)_3(Ga,Al)_5O_{12}$ Single-Crystal Scintillators", K. Kamada et al, Cryst. Growth Des., 2011, 11 (10), pp 4484-4490 for a crystal garnet composition. As can be seen with reference to the table in FIG. 1, increasing the parameter y, thus replacing Gd with Lu in a single crystal garnet composition having $Al_2$ significantly degrades the light yield from 42217 photons/MeV in row 1 to 18166 photons/MeV in row 5, thus to 43% as compared to an otherwise unchanged $Gd_3Ga_3Al_2O_{12}$ composition. By contrast, as described above, the effect of the same increase in parameter y in the ceramic composition of the present invention, thus replacing Gd with Lu, is that the light yield is 82% of the single crystal reference composition $Gd_3Ga_3Al_2O_{12}$. The light yield in the ceramic composition $Lu_1Gd_2Ga_3Al_2O_{12}$ is therefore approximately a factor of 2 higher than would be expected based on the prior art single crystal composition $Lu_1Gd_2Ga_3Al_2O_{12}$ and represents a significant improvement in performance in the scintillator material field.

Such a result is even more unexpected in view of ceramic scintillator materials being considered to have significantly degraded light yields as compared to their crystal counterparts.

The significance of the high light yield in the ceramic composition $Lu_1Gd_2Ga_3Al_2O_{12}$ is that thermal quenching does not occur to the same degree in the high gallium-content ceramic compositions of the present invention as would be expected from a single crystal composition. This is confirmed by the short primary decay constant $\tau_1$ in the ceramic composition in the table in FIG. 2. Thermal quenching reduces both the light yield and the decay time and is observed in the single crystal prior art compositions in the progression between row 1 through 3 in the table in FIG. 1. Throughout this progression the gradual increase in the ratio of gallium to aluminium, parameter x, results in a reduced primary decay constant $\tau_1$ and a reduced light yield. That the light yield remains high in the ceramic composition in FIG. 2 is indicative of reduced thermal quenching in this high gallium content ceramic composition.

Figure 3A:
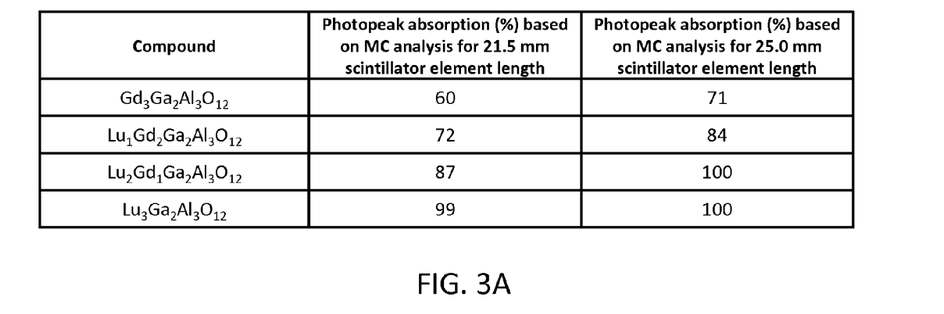
FIG. 3A illustrates Monte Carlo simulation results of the effect of varying the lutetium content on the photopeak absorption in various ceramic garnet compositions.

The parameter y in the garnet scintillator composition affects the ratio of lutetium to gadolinium. FIG. 3A illustrates Monte Carlo simulation results of the effect of varying the lutetium content on the photopeak absorption in various ceramic garnet compositions. The photopeak absorption, recorded here as a percentage, is the fraction of the original 511 keV energy of an incident gamma photon energy that is deposited in the photopeak. A high percentage of photopeak absorption is desirable because it permits the discrimination of incident gamma photons based on their energy. This in turn allows for the rejection of gamma photons which have undergone energy-altering scattering, an aspect which finds particular benefits in the process of assigning LORs to pairs of simultaneously-detected gamma photons in a PET imaging system. From FIG. 3A it can be seen that the percentage of photopeak absorption increases as the amount of lutetium in the composition, thus the parameter y, is increased. Increasing the length of the scintillator element also increases the photopeak absorption at the expense of an increased volume of scintillator material.

Figure 3B:
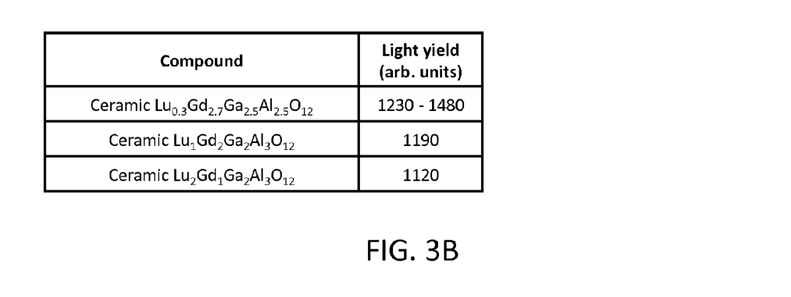
FIG. 3B illustrates the effect of varying the lutetium content, thus the parameter y, on the measured light yield in various ceramic garnet compositions.

FIG. 3B illustrates the effect of varying the lutetium content, thus the parameter y, on the measured light yield in various ceramic garnet compositions. From FIG. 3B it can be seen that increasing the amount of lutetium in the composition, thus the parameter y, has the effect of decreasing the light yield. Low values of lutetium content are therefore preferred because ultimately it is the light yield that affects scintillator sensitivity.

Together, FIGS. 3A and 3B are indicative of a range y=1 350.5 wherein both high photopeak absorption and high light yield are achieved. Narrowing the range to y=1±0.25 results in even further improved performance, and narrowing the range to y=1±0.1 results in the highest performance.

Figure 4:
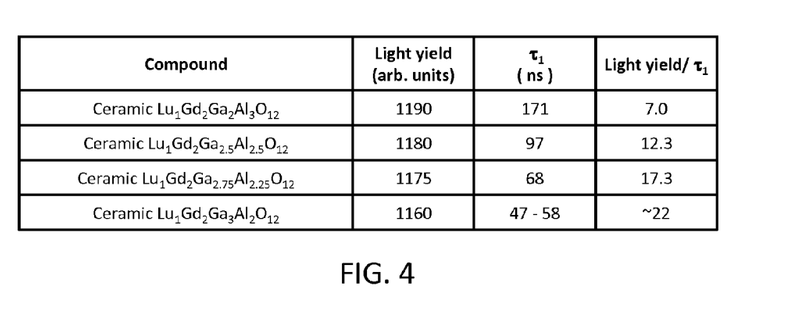
FIG. 4 illustrates the effect of varying the gallium content, thus the parameter x, on the measured light yield and the measured primary decay constant $\tau_1$ in various ceramic garnet compositions.

The parameter x in the garnet scintillator composition affects the ratio of gallium to aluminium. FIG. 4 illustrates the effect of varying the gallium content, thus the parameter x, on the measured light yield and the measured primary decay constant $\tau_1$ in various ceramic garnet compositions. As described above, a high light yield improves the signal to noise ratio at the output of the optical detector, and a short decay time is important in the prevention of pile-up. As the gallium content is increased in the table in FIG. 4, both the light yield and the decay time can be seen to decrease, and the decay time decreases at a much faster rate. The ratio of the light yield to the decay time is also plotted in the table in FIG. 4, and this may be seen as a quality parameter that is desirably maximized. In order to increase the value of the ratio of the light yield to the decay time, FIG. 4 points to the use of garnet compositions having high gallium content, thus a high value of x. However this benefit diminishes when the light yield falls to unacceptably low levels. Consequently there is a range x=3±0.25 within which high light yield and a short decay time can be achieved together. Narrowing the range to x=3±0.1 results in even further improved performance, and narrowing the range to x=3±0.01 results in the highest performance.

The cerium content claimed in the garnet scintillator composition of the present invention is preferably in the range 0.1 mol % to 0.7 mol %. Cerium is the dopant that gives rise to the light emission from the garnet host. Consequently a minimum cerium content is required for light emission.

Figure 5:
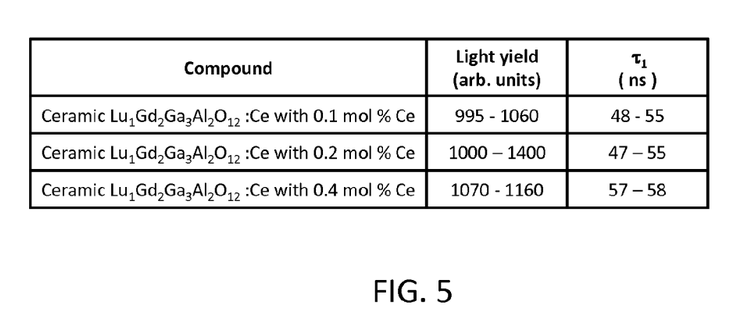
FIG. 5 illustrates the effect of varying the cerium content, on the measured light yield and the measured primary decay constant $\tau_1$ in various ceramic garnet compositions.

FIG. 5 illustrates the effect of varying the cerium content, on the measured light yield and the measured primary decay constant $\tau_1$ in various ceramic garnet compositions. From FIG. 5 it can be seen that increasing the cerium content from 0.1 mol % to 0.4 mol % results in a slight increase in the light yield and a slight increase in the primary decay constant $\tau_1$.

Figure 6:
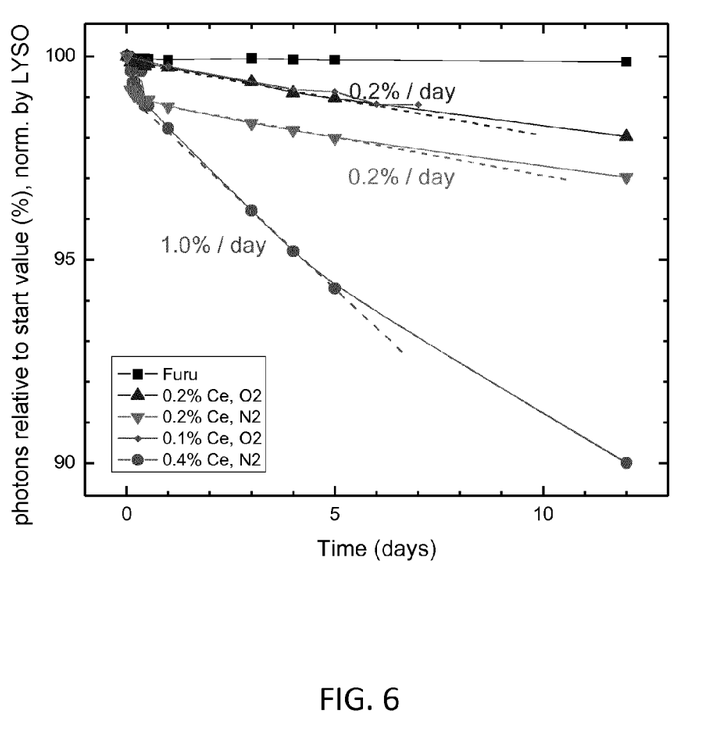
FIG. 6 illustrates the effect of varying the cerium content on the stability of the light yield measured in various garnet compositions having different cerium concentrations.

FIG. 6 illustrates the effect of varying the cerium content on the stability of the light yield measured in various garnet compositions having different cerium concentrations. In FIG. 6 measurements of the total number of optical photons generated in the scintillator composition by a 511 keV gamma photon are recorded for various garnet compositions at different points in time. The initial number of photons generated in each composition is indicated by the first 100% data point on the left hand side of the graph. Subsequent measurements of the number of photons thus generated in that composition are scaled to this initial value. Immediately after the measurement at Time=0, the signal decays strongly during a time span of a two hours. This is an effect of the afterglow seen after strong illumination with visible light during the mounting of samples, or after a strong x-ray pulse. Subsequent measurements indicate the total number of optical photons generated in the scintillator composition by a 511 keV gamma photon. The curve marked Furu in FIG. 6 corresponds to the reference single crystal sample single crystal $Gd_3Ga_3Al_2O_{12}$ the results of which are shown in the first line of FIG. 2. All other results in FIG. 6 are for ceramic garnet compositions $Lu_1Gd_2Ga_3Al_2O_{12}$. One sample has 0.4 mol % cerium, two other samples each have 0.2 mol % cerium, and a fourth sample has 0.1 mol % Ce. From FIG. 6 it can be seen that ceramic garnet compositions having 0.4 mol % cerium exhibit a degradation in the relative number of photons generated in the scintillator composition by a 511 keV gamma photon. The sample with 0.4 mol % cerium exhibits a degradation of 1.0% per day, and is therefore more unstable than samples that have 0.1-0.2 mol % cerium. Differences in annealing conditions between the two samples with 0.2 mol % cerium, wherein one was annealed in oxygen and the other in nitrogen appeared to have negligible effect on the measured stability, only on the short term afterglow effect. Consequently when taken together, FIGS. 5 and 6 indicate that a short decay time and a high light yield can be achieved in a stable garnet scintillator composition when the cerium content is in the range 0.1 mol % to 0.2 mol %. A cerium content range 0.1 mol % to 0.3 mol % is anticipated to give acceptable stability results.

Figure 7:
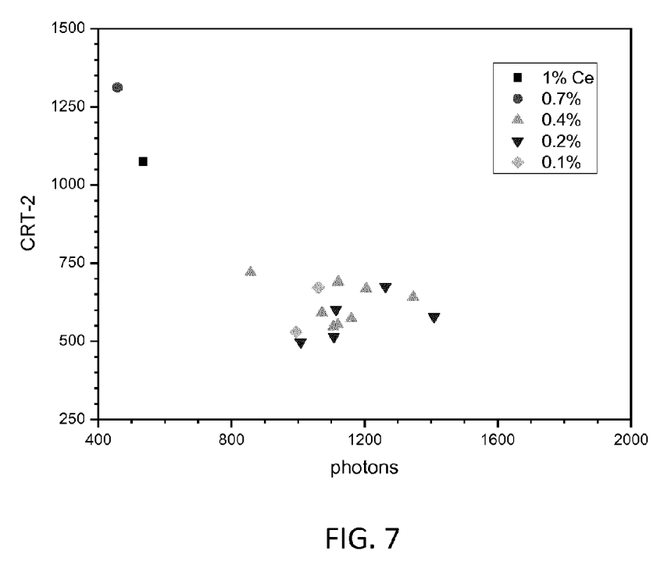
FIG. 7 illustrates measurements of the Coincidence Resolving Time (CRT-2) and light yield (photons) for various mol (%) cerium dopant concentrations.

FIG. 7 illustrates measurements of the Coincidence Resolving Time (CRT-2) and light yield (photons) for various mol (%) cerium dopant concentrations. A low CRT and high light yield are desirable in optimizing the sensitivity of the garnet composition for use in a PET imaging system. From FIG. 7 it can be seen that a high light yield and a low CRT can be achieved in garnet scintillator compositions having a cerium content in the range 0.1 to 0.4 mol %.

Advantageously the ceramic composition of the present invention lends itself to simpler fabrication processes than single crystal compositions, thereby reducing fabrication costs. The ability to form ceramic materials using pressing processes furthermore improves the freedom to manufacture scintillator compositions with bespoke shapes and with less waste as compared to single crystal manufacture methods. Furthermore, by replacing some of the element gadolinium with the cheaper element lutetium, the cost of the composition may be reduced.

The scintillator compositions of the present invention were prepared according to conventional ceramic fabrication techniques. High purity raw materials, 4N or better, of $Lu_2O_3$, $Gd_2O_3$, $Al_2O_3$, $Ga_2O_3$ and $CeO_2$ were weighed and mixed in water in a jar using 2 mm $Al_2O_3$ balls. After mixing, the slurry was dried and granulated. Samples were then dry-pressed. Following binder burn out the samples were sintered at a temperature in the range 1650 to 1750° C. in a vacuum furnace Annealing in an oxygen containing atmosphere was performed after sintering, wherein temperatures of 1000-1600° C. were found suitable. The samples were subsequently characterized after grinding and polishing the annealed samples.

The light yield that was measured in the embodiments illustrated in the Figures was determined in accordance with the following procedure: The polished samples were assembled into an array of garnet sticks covered with reflector sheets. This array was optically coupled to an array of silicon photomultipliers (Philips Digital Photon Counters) using Cargille Meltmount, with the photomultiplier pixels and the garnet sticks in a one-to-one correspondence. A sealed Na-22 radioactive source was brought at 10 cm distance above the garnet sticks of the array, with another scintillator array at 10 cm distance above the Na-22 source so that measurements on both arrays in coincidence were enabled. During a time span of approximately five minutes the photon gain after absorption of 511 keV gamma quanta was repetitively measured and averaged.

The CRT that was measured in the embodiments illustrated in the Figures was determined using the same measurement setup. The Philips Digital Photon Counter provides measurement data of the number of photons counted and the time stamp of the measurement. Coincident events measured on pairs of scintillator sticks on both arrays were evaluated in terms of the coincidence resolving time. The statistical distribution of the CRT for all pairs of scintillator sticks was averaged to obtain the CRT for each type of garnet stick.

The decay time that was measured in the embodiments illustrated in the Figures was determined in accordance with the following procedure: A single garnet stick was covered by reflective sheets on five faces and optically mounted to a photomultiplier face plate using silicone gel. A Na-22 radioactive source and a second photomultiplier were arranged to enable measurements in coincidence. Electrical signals from the photomultipliers, triggered by the gamma quanta measured on one of the photomultipliers, were read out by a digital storage oscilloscope (LeCroy). During a time span of about one hour the photomultiplier signal after absorption of 511 keV gamma quanta was measured, stored, corrected for spurious signals, averaged and evaluated to determine the decay time constant.

The various embodiments of the invention described herein are now described with reference to their exemplary use in gamma photon detection and in a PET imaging system.

Figure 8:
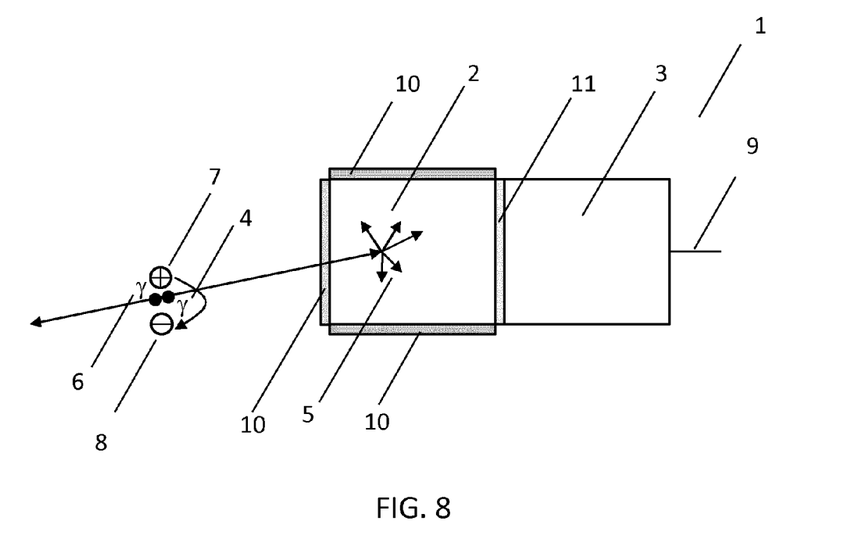
FIG. 8 illustrates an exemplary gamma photon detector 1 in which the scintillator composition of the present invention may be used.

FIG. 8 illustrates an exemplary gamma photon detector 1 in which the scintillator composition of the present invention may be used. In FIG. 8, gamma photon detector 1 comprising scintillator composition 2 and optical detector 3 are in optical communication. The optical detector may be for example a PMT or a solid state semiconductor optical detector such as a silicon avalanche photodiode (Si APD) or a silicon photomultipliers (SiPM), and operates to convert optical radiation into electrical signals. Desirably the sensitivity of the optical detector is matched to the characteristic range of scintillation wavelengths emitted by the scintillator composition. When in use, the reception of gamma photon 4 by scintillator composition 2 results in the generation of scintillation light 5 comprising a plurality of photons having frequencies corresponding to the characteristic range of scintillation wavelengths of scintillator composition 2. Typically the photons in the scintillation light 5 have energies that are much smaller than that of the captured gamma photon 4 and thus the scintillation light may comprise optical wavelengths from the UV through the visible to the infrared region. Subsequently a portion of the scintillation light 5 is captured by optical detector 3, resulting in an electrical signal at optical detector output 9 that is indicative of the capture of gamma photon 4. The electrical signal may subsequently be processed by electrical circuitry. Gamma photon 4 may be one of a pair of oppositely directed gamma photons 4, 6. The pair of gamma photons may be formed as a consequence of an annihilation event following radioactive decay, wherein the radioactive decay produces positron 7 and is annihilated by electron 8. The source of the radioactive decay may be for example a radiotracer. Optical coatings 10 such as reflective layers may be used on one or more faces of the scintillator composition 2 other than those in optical communication with the optical detector in order to retain the scintillation light 5 so as to increase the portion of the scintillation light captured by optical detector 3. An interface coating 11 may be disposed between scintillator composition 2 and optical detector 3, such as an antireflection coating or an index matching coating, in order to improve the portion of scintillation light 5 captured by optical detector 3.

Figure 9:
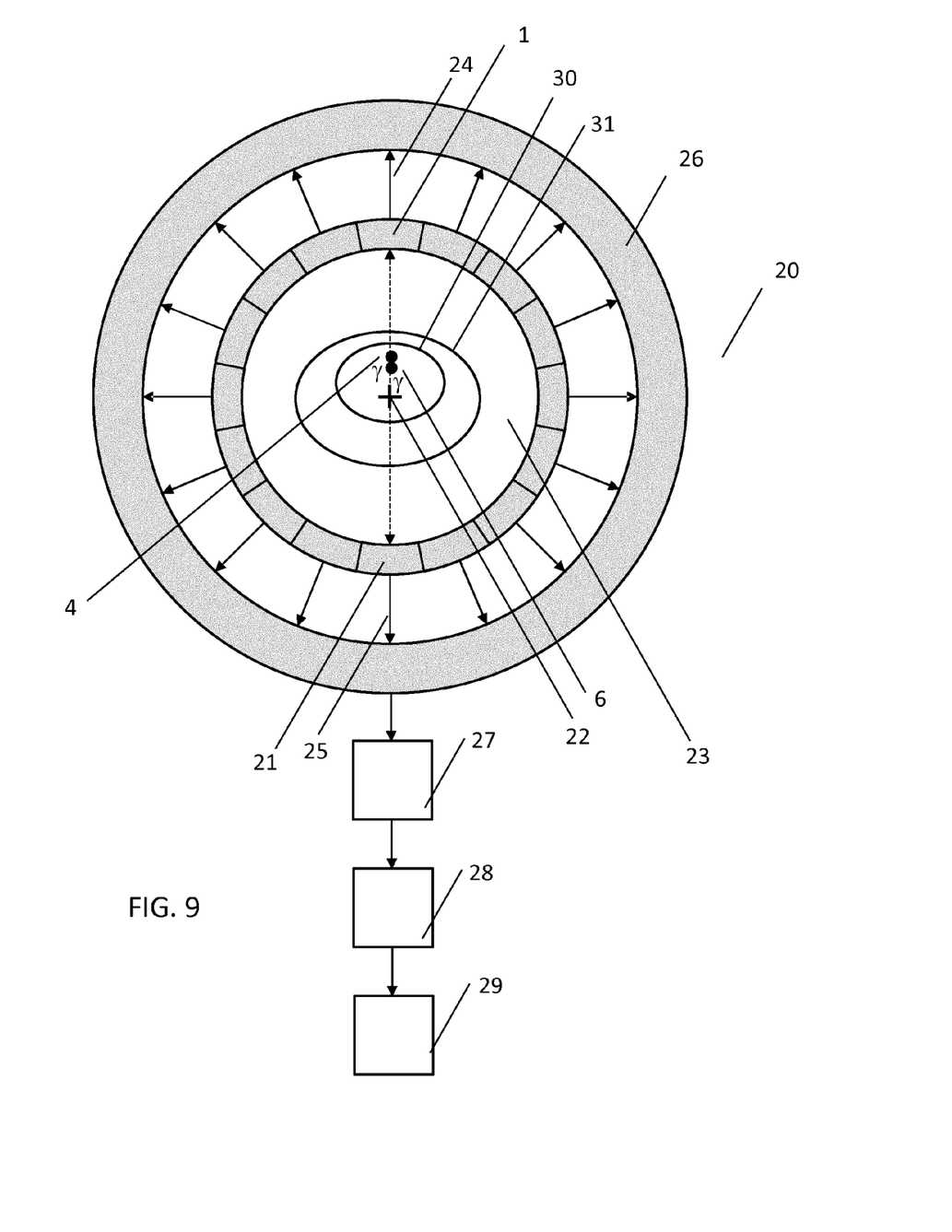
FIG. 9 illustrates an exemplary PET imaging system 20 in accordance with certain aspects of the invention.

FIG. 9 illustrates an exemplary PET imaging system 20 in accordance with certain aspects of the invention. The exemplary gamma photon detector of FIG. 8 may for example be used in the system illustrated in FIG. 9. In FIG. 9, PET imaging system 20 comprises two or more gamma photon detectors 1, 21 disposed radially about axis 22 of an imaging region 23. In this configuration axis 22 is the longitudinal axis of the imaging region. The two or more gamma photon detectors 1, 21 each produce electrical signals at their corresponding optical detector outputs 24, 25 indicative of received gamma photons. Optical detector outputs 24, 25 are in electrical communication with coincidence determination unit 26. Coincidence determination unit 26 assesses the temporal coincidence of pairs of gamma photons based on the electrical signals from optical detector outputs 24, 25. Coincidence determination unit 26 may assign a timestamp to each electrical signal 24, 25 that meets a predetermine threshold condition and deem two gamma photons as coincident if their electrical signals, or timestamps occur within a narrow time interval, typically +/−3 ns, of each other. Coincidence determination unit 26 may also analyze the energy of each captured photon, for example by integrating the electrical signal and thus the light pulse generated in the scintillator composition by a gamma photon, and deem two photons as coincident if they both occur within a narrow time interval as well as have energies within a narrow energy window, typically within +/−10% of a peak gamma photon energy. Coincidence determination unit 26 may also compute the depth of interaction (DOI) of a gamma photon in the scintillator composition based on for example the spatial distribution of its scintillation light across an array of optical detectors. The DOI may be used to reject temporally coincident gamma photons whose DOI is indicative of gamma photon scattering. Coincidence determination unit 26 is in communication with reconstruction processor 27 which is configured to construct a line of response for each pair of captured photons deemed coincident and to further process multiple such lines of response in order to reconstruct data representing an image comprising the originating positions of the captured photons deemed coincident by coincidence determination unit 26. In a TOF PET imaging system having improved timing accuracy, thus an improved CRT, the exact time of detection of each gamma photon may further be used to localize the position along the line of response at which the two gamma photons 4, 6 were generated and thereby improve the quality of the reconstructed image. Reconstruction processor 27 is in communication with image processing unit 28 which is configured to process the data representing the originating positions of the coincident photons into a format suitable for presenting an image on an output device. Image processing unit 28 is in further communication with an output device 29 for presenting the image, such as a display, a printer and the like.

When in use, a portion 30 of a subject to be imaged 31, such as portion of a human or animal body is positioned in imaging region 23 of the exemplary PET imaging system in FIG. 9. The portion 30 may represent a region such as an organ within the subject in which it is desired to measure the uptake of a radiotracer. Prior to the positioning of the portion 30 of the subject to be imaged 31 in the imaging region 23, a radiotracer may be administered to the subject, and an uptake period may be permitted to lapse prior to the commencement of imaging. During the imaging process the two or more gamma photon detectors 1, 21 capture gamma photons resulting from radioactive decay events within imaging region 23, such as from the decay of a radiotracer administered to a subject. A common radiotracer used in PET imaging is fludeoxyglucose, FDG, an analogue of glucose that is labelled with fluorine-18 and whose decay results in pairs of gamma photons each having an energy of 511 keV. Following the imaging process the PET imaging system produces an image indicative of the distribution of the radiotracer within portion 30 of the subject to be imaged 31.

The exemplary PET imaging system 20 may also be arranged co-axially with a second imaging system such as a CT or an MR imaging system such that simultaneous or sequential imaging by the PET imaging system and the CT or MR imaging system may take place. The PET and second imaging systems may have axially-separated imaging regions, or share a common imaging region from which imaging data is collected by the two imaging systems.

Figure 10:
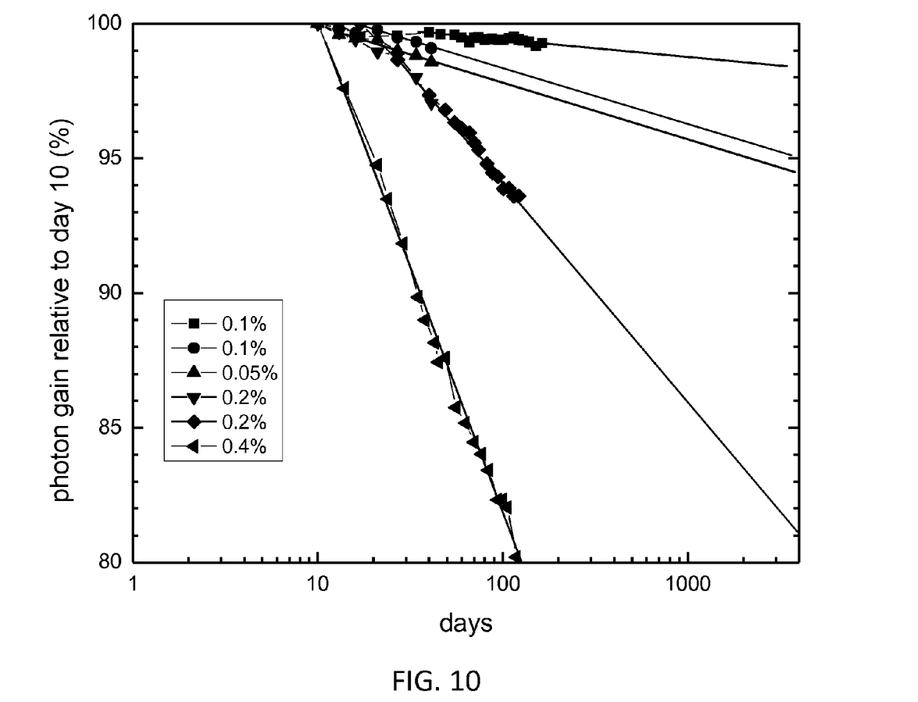
FIG. 10 illustrates the effect of varying the cerium content on the stability of the light yield measured in various ceramic garnet compositions represented by the formula $Lu_1Gd_2Ga_3Al_2O_{12}$:Ce.
Figure 11:
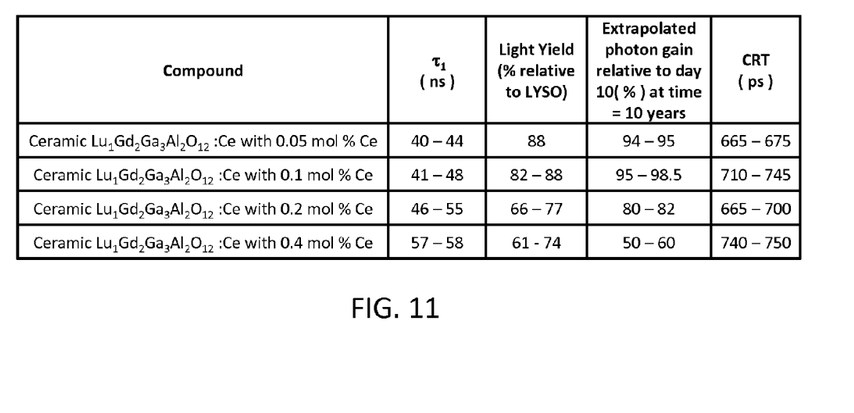
FIG. 11 illustrates the effect of varying the cerium content on the measured primary decay constant $\tau_1$, and on the measured light yield relative to a reference LYSO sample, and on the extrapolated photon gain relative to day 10 at time =10 years, and on the measured coincidence resolving time (CRT), in various ceramic garnet compositions represented by the formula $Lu_1Gd_2Ga_3Al_2O_{12}$:Ce.

FIG. 10 illustrates the effect of varying the cerium content on the stability of the light yield measured in various ceramic garnet compositions represented by the formula $Lu_1Gd_2Ga_3Al_2O_{12}$:Ce. Each trace in FIG. 10 represents the light yield at a given time, as a percentage of the light yield provided by the same sample on the $10^{th}$ day since its production. The horizontal axis titled Days represents the number of days since production of the sample. Measurements from a 0.05 mol % Ce ceramic garnet are shown in FIG. 10, demonstrating that high light yield stability is also achieved at lower cerium concentrations than those shown in FIG. 6. FIG. 11 illustrates the effect of varying the cerium content on the measured primary decay constant $\tau_1$, and on the measured light yield relative to a reference LYSO sample, and on the extrapolated photon gain relative to day 10 at time =10 years, and on the measured coincidence resolving time (CRT), in various ceramic garnet compositions represented by the formula $Lu_1Gd_2Ga_3Al_2O_{12}$:Ce. The Extrapolated photon gain relative to day 10 at time =10 years recorded in FIG. 11 was obtained by extrapolating the measurements in FIG. 10 to a time of 10 years and noting the value of the y-axis. FIG. 11 includes measurements from a 0.05 mol % Ce ceramic garnet and demonstrates that a short primary decay constant, a high light yield, a highly stable light yield, and a short coincidence resolving time are all provided by the 0.05 mol % Ce ceramic garnet composition.

Taken together, the results of FIGS. 1 to 7, and 10 to 11 indicate a preference for a cerium content in the range 0.05 mol % to 0.7 mol %, although the range 0.01 mol % to 0.7 mol % is also expected to be acceptable. Narrowing the range to 0.01 mol % to 0.4 mol %, or 0.05 mol % to 0.4 mol % offers compositions with a short primary decay constant and improved light yield and improved coincidence resolving time. Narrowing the range further to 0.01 mol % to 0.2 mol %, or 0.05 mol % to 0.2 mol % offers compositions with improved light yield stability.

To summarize, a ceramic or polycrystalline scintillator composition represented by the formula $(Lu_yGd_{3-y})(Ga_xAl_{5-x}O_{12})$:Ce; wherein $y=1\pm0.5$; wherein $x=3\pm0.25$; and wherein Ce is in the range 0.1 mol % to 0.7 mol % is disclosed herein. The composition has improved sensitivity in terms of its light yield, decay time, and its ceramic or polycrystalline form advantageously lends itself to simpler manufacturing processes as compared to single crystal compositions. The scintillator composition finds application in the sensitive detection of ionizing radiation and may for example be used in the detection of gamma photons in the field of PET imaging wherein the reduced CRT advantageously provides more accurate PET images.

Whilst the invention has been illustrated and described in detail in the drawings and foregoing description, such illustrations and description are to be considered illustrative or exemplary and not restrictive; the invention is not limited to the disclosed embodiments and can be used in the detection of ionizing radiation in various application fields.

The invention claimed is:

1. A ceramic or polycrystalline garnet scintillator composition represented by the formula $(Lu_yGd_{3-y})(Ga_xAl_{5-x})O_{12}$:Ce;
   wherein $y=1\pm0.5$;
   wherein $x=3\pm0.25$; and
   wherein Ce is in the range 0.01 mol % to 0.7 mol %.

2. The scintillator composition of claim 1 wherein Ce is in the range 0.05 mol % to 0.7 mol %.

3. The scintillator composition of claim 1 wherein Ce is in the range 0.1 mol % to 0.7 mol %.

4. The scintillator composition of claim 1 wherein Ce is in the range 0.05 mol % to 0.2 mol %.

5. The scintillator composition of claim 1 wherein Ce is in the range 0.1 mol % to 0.2 mol %.

6. The scintillator composition of claim 4 having a primary decay constant of less than or equal to 55 ns.

7. A ceramic or polycrystalline scintillator composition represented by the formula $(Lu_yGd_{3-y})(Ga_xAl_{5-x})O_{12}$:Ce;
   wherein $y=1\pm0.5$;
   wherein $x=3\pm0.25$; and
   wherein Ce is in the range 0.05 mol % to 0.2 mol %;
   having a primary decay constant of less than or equal to 55 ns;
   having a light yield exceeding 30000 photons/MeV.

8. A gamma photon detector comprising the scintillator composition according to claim 1 in optical communication with an optical detector.

9. A detector for detecting ionizing radiation comprising the scintillator composition according to claim 1 in optical communication with an optical detector.

10. A PET imaging system having an imaging region and comprising a plurality of gamma photon detectors according to claim 8;
    wherein the plurality of gamma photon detectors are disposed radially about an axis of the imaging region and are configured to receive gamma photons from the imaging region.

11. A Time of Flight PET imaging system comprising a plurality of gamma photon detectors disposed radially about an axis of the imaging region and configured to receive gamma photons from the imaging region, each gamma photon detector including a ceramic or polycrystalline garnet scintillator composition in optical communication with an optical detector, the ceramic or polycrystalline garnet scintillator composition represented by the formula $(Lu_yGd_{3-y})(Ga_xAl_{5-x})O_{12}$:Ce;
    wherein $y=1\pm0.5$;
    wherein $x=3\pm0.25$; and
    wherein Ce is in the range 0.01 mol % to 0.7 mol %; and timing circuitry configured to localize an originating position of a decay event in the imaging region by computing a time difference between pairs of gamma photons generated by the decay event and which are received substantially coincidently by the gamma photon detectors.

12. A PET imaging system according to claim 10 having a coincidence resolving time of less than 750 ns.

13. A combined imaging system comprising the imaging system of claim 10 and a second imaging system;
wherein the second imaging system has an imaging region that is either axially separated from an axis of the imaging region of the PET imaging system, or is coincident with the imaging region of the PET imaging system.

14. The combined imaging system of claim 13 wherein the second imaging system is a Computed Tomography, an MR or an Ultrasound imaging system.

15. A method of detecting a gamma photon comprising the steps of:

receiving a gamma photon with the scintillator composition according to claim 1;
detecting scintillation light generated by the scintillator composition using an optical detector in optical communication with the scintillator composition; and
generating an electrical output from the optical detector in response to the received gamma photon.

16. A method of generating a PET image indicative of the distribution of a radiotracer within an imaging region; the method comprising the steps of:
administering a radiotracer to a subject;
waiting for a predefined uptake period after administering the radiotracer; and
imaging at least a portion of the subject with the PET imaging system of claim 10.

17. The scintillator composition of claim 4 wherein the composition is a sintered ceramic composition.

18. The scintillator composition of claim 4 having a light yield exceeding 30000 photons/MeV.

* * * * *